(12) United States Patent
Howell et al.

(10) Patent No.: US 9,039,675 B2
(45) Date of Patent: May 26, 2015

(54) I.V. INFUSION OR BLOOD COLLECTION APPARATUS

(75) Inventors: Julie C. Howell, Indian Trail, NC (US); Michael A. Taylor, Apex, NC (US); John F. Higdon, Matthews, NC (US); Robert G. Rosenthal, Raleigh, NC (US); Sanjiv Kumar, Apex, NC (US)

(73) Assignee: MDDP, LLC, Cary, NC (US)

( * ) Notice: Subject to any disclaimer, the term of this patent is extended or adjusted under 35 U.S.C. 154(b) by 121 days.

(21) Appl. No.: 13/810,326

(22) PCT Filed: Jul. 15, 2011

(86) PCT No.: PCT/US2011/044114
§ 371 (c)(1),
(2), (4) Date: Jan. 15, 2013

(87) PCT Pub. No.: WO2012/009599
PCT Pub. Date: Jan. 19, 2012

(65) Prior Publication Data
US 2013/0116598 A1  May 9, 2013

Related U.S. Application Data

(60) Provisional application No. 61/399,629, filed on Jul. 15, 2010.

(51) Int. Cl.
*A61B 5/15* (2006.01)
*A61B 5/153* (2006.01)
(Continued)

(52) U.S. Cl.
CPC ......... *A61B 5/150641* (2013.01); *A61B 5/1405* (2013.01); *A61B 5/15003* (2013.01);
(Continued)

(58) Field of Classification Search
CPC ...................... A61M 25/0631; A61M 25/0637; A61M 5/3271; A61M 5/3257; A61M 25/0612; A61M 25/02

USPC .................. 604/110, 177, 174, 192, 198, 263
See application file for complete search history.

(56) References Cited

U.S. PATENT DOCUMENTS

| 5,120,320 A | 6/1992 | Fayngold |
| 2007/0088262 A1 | 4/2007 | Jones et al. |

FOREIGN PATENT DOCUMENTS

CN  101330937 A  12/2008

OTHER PUBLICATIONS

International Search Report and Written Opinion for PCT/US2011/044114 mailed Nov. 14, 2011, 13 pages.
(Continued)

*Primary Examiner* — Rebecca E Eisenberg
(74) *Attorney, Agent, or Firm* — Withrow & Terranova, PLLC

(57) ABSTRACT

An I.V. infusion or blood collection apparatus comprises an I.V. infusion set (100) and a safety shield (200). The I.V. infusion set has a wing body (105) from which a pair of wings (140) extend outward there from and a grip (145) extending upward there from. One end of the wing body mounts a needle (120) or catheter and medical tubing (130) is connected to the opposite end. The wing body includes a bore so that fluid flows between the needle and the medical tubing. A safety shield has a top, a bottom and opposing side walls and defines a cavity (227) that is adapted to receive the I.V. infusion set. The safety shield has slots (250) in each of the side walls and a slot (255) in the top. The respective wings and grip are adapted to be positioned in the slots and to slidably move therein. The slot in the top includes a lock that is adapted to receive the grip so that when the needle is retracted into the cavity; the grip is permanently captured therein, thus locking the needle in the fully retracted safety position.

21 Claims, 21 Drawing Sheets

(51) Int. Cl.
*A61M 5/158* (2006.01)
*A61M 5/32* (2006.01)
*A61M 25/06* (2006.01)

(52) U.S. Cl.
CPC ..... *A61B5/150259* (2013.01); *A61B 5/150389* (2013.01); *A61B 5/150519* (2013.01); *A61B 5/15074* (2013.01); *A61B 5/150916* (2013.01); *A61B 5/153* (2013.01); *A61M 5/158* (2013.01); *A61M 5/3271* (2013.01); *A61M 25/0606* (2013.01); *A61M 25/0631* (2013.01); *A61M 25/0637* (2013.01); *A61M 2005/1586* (2013.01); *A61M 2005/3247* (2013.01); *A61M 5/3221* (2013.01)

(56) References Cited

OTHER PUBLICATIONS

First Office Action in Chinese Patent Application No. 201180044609.3 with English translation, mailed Jul. 24, 2014, 22 pages.

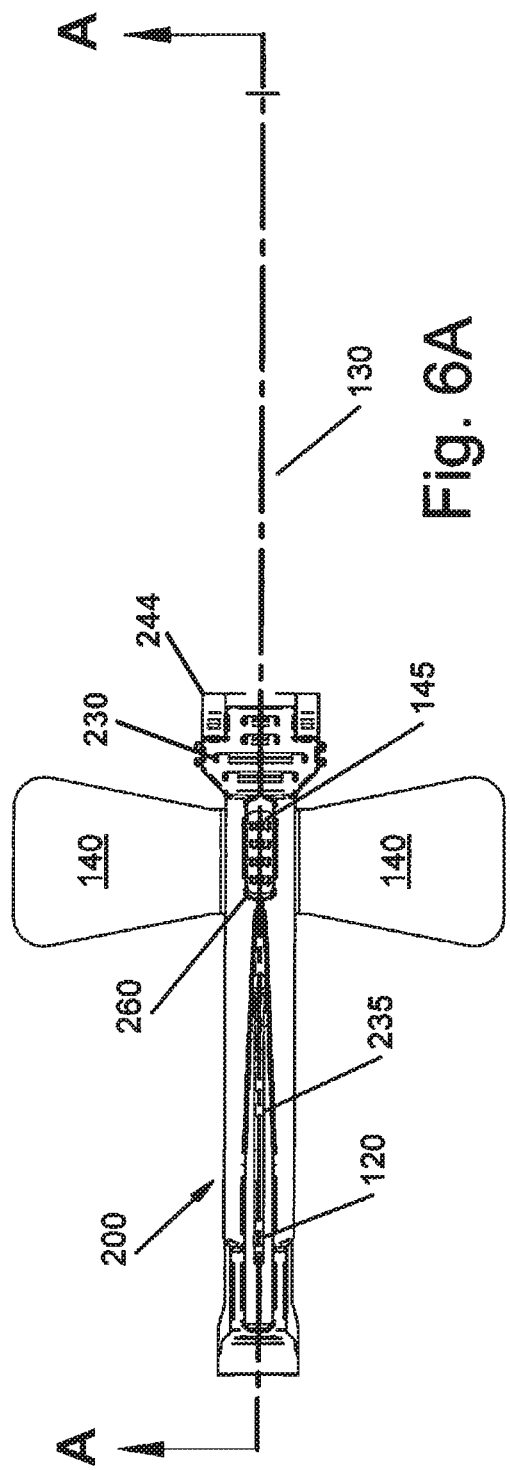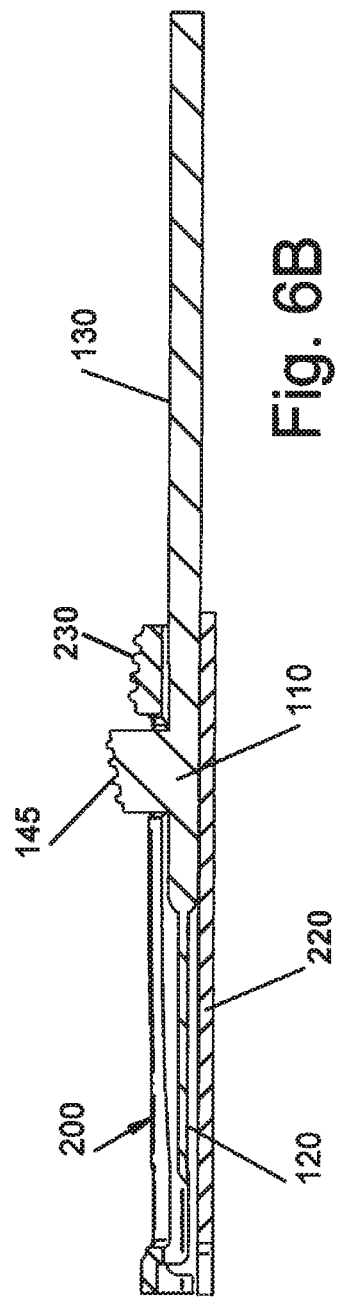

I.V. INFUSION OR BLOOD COLLECTION APPARATUS

PRIORITY CLAIM

This application is a 35 USC 371 National Phase filing based on and claiming priority to International Application No. PCT/US2011/044114 filed Jul. 15, 2011, which claims the benefit of U.S. Provisional Patent Application Ser. No. 61/399,629 filed Jul. 15, 2010, both of which are incorporated by reference herein in their entireties.

FIELD OF THE INVENTION

This invention relates generally to the field of medical devices and more particularly to the field of safety products used for blood collection or infusion to prevent accidental needle sticks.

BACKGROUND OF THE INVENTION

The collection of blood from a patient or infusion into a patient are two of the most commonly performed medical procedures in the world. Blood collection is necessary in order to evaluate the chemical constituency of the bodily functions in order to diagnose medical conditions and to validate treatment plans and infusion is necessary to deliver pharmaceuticals, ringers or other preparations in liquid form. Notwithstanding the foregoing, injuries caused by needles and other sharp medical devices and the related risk of potentially fatal disease transmission remain a major threat to the health and safety of health care workers around the world. In addition, the distress, sickness and absenteeism resulting from sharps injuries constitute a considerable strain on the already limited human resources in the medical profession.

The majority of sharps injuries are suffered by nurses and occur in patient rooms and the operating theatre, but doctors, dentists and other medical staff are also victims. Ancillary staff such as cleaners and laundry staff and other downstream workers, are also at risk.

The term "needle stick" injury has come to be the term used to describe inadvertent penetration of the skin by a previously used, contaminated catheter, needle or other percutaneous device. A combination of training, safer working practices and the use of medical devices incorporating needle stick protection technology can prevent many of these potentially serious injuries.

The U.S. Congress took action in response to growing concerns over blood borne pathogen exposures from sharps injuries and in response to recent technological developments that increased employee protection. On Nov. 6, 2000, the "Needle Stick Safety and Prevention Act" was signed into law, requiring that all health care facilities in the U.S. evaluate, purchase and provide medical devices incorporating needle protection for their staff. Health care employers in the U.S. are also now required to maintain a sharps injury log and involve non-managerial potentially exposed health care workers in the evaluation and implementation of work practice controls and devices incorporating needle protection.

Thus, safe disposal of sharp medical instruments, such as scalpel blades and syringe needles has become an important issue, addressed at the highest level of the U.S. government, due to the possible transmission of disease by accidental skin-penetrating contact during disposal of sharp medical instruments, commonly known as "medical sharps."

There are several scenarios that describe the accidental needle stick injury: First, a handler may be stuck by a syringe needle while attempting to re-cap the needle after it has been used. Second, a handler may be stuck by a syringe needle while transporting it to a proper "Sharps Container." Third, a handler or other individuals may be stuck when contacting a syringe and needle that has been left unprotected and unattended. Fourth, individuals that transport medical waste may be stuck by unprotected, uncapped or improperly stored syringes and needles.

In general, it is considered "unsafe" to re-cap a syringe needle due to the extreme possibility that the handler will be stuck by the needle while re-capping and the present invention presents an improved safety system for preventing sharps injuries in connection with blood collection sets.

It is thus an object of the invention to provide an improved I.V. infusion or blood collection apparatus.

It is a further object of the present invention to provide an improved I.V. infusion or blood collection apparatus having enhanced safety features.

A still further object of the present invention is to provide an improved I.V. infusion or blood collection apparatus that is easy to use and inexpensive to produce.

These and other objects will become apparent when taken in connection with the accompanying drawings.

DESCRIPTION OF THE DRAWINGS

FIG. 6A is a plan view, partially broken away of the blood collection set according to the present invention illustrating the needle in the retracted position.

FIG. 6B is a sectional view of the blood collection set according to the present invention taken along line A-A of FIG. 6A illustrating the needle in the retracted position.

SUMMARY OF THE INVENTION

Figure 1:
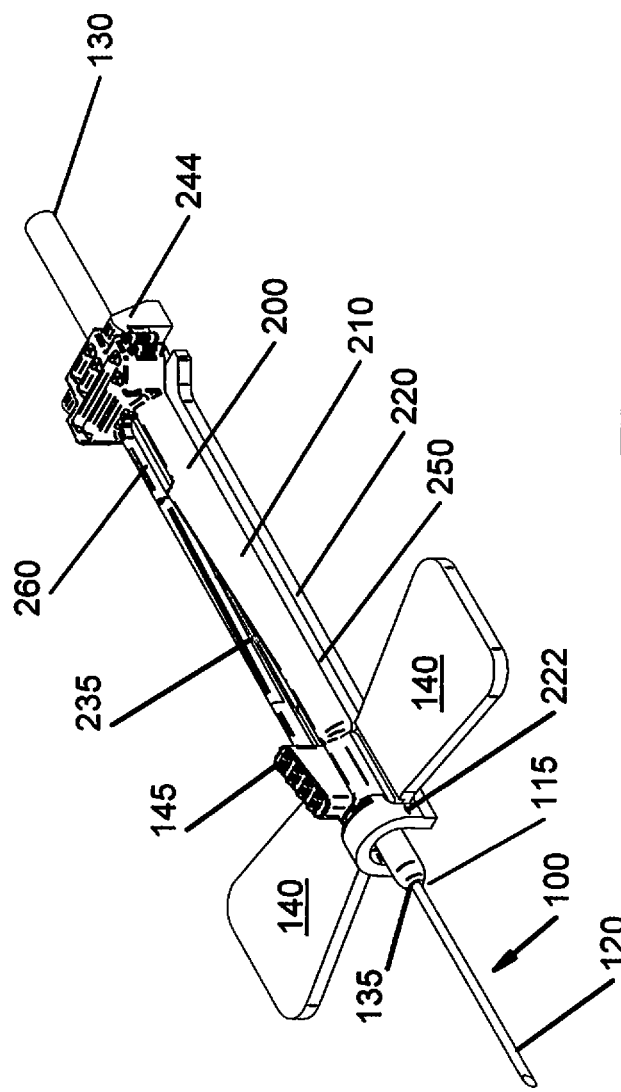
FIG. 1 is a perspective view of the blood collection set according to the present invention illustrating the needle in the extended position.
Figure 2:
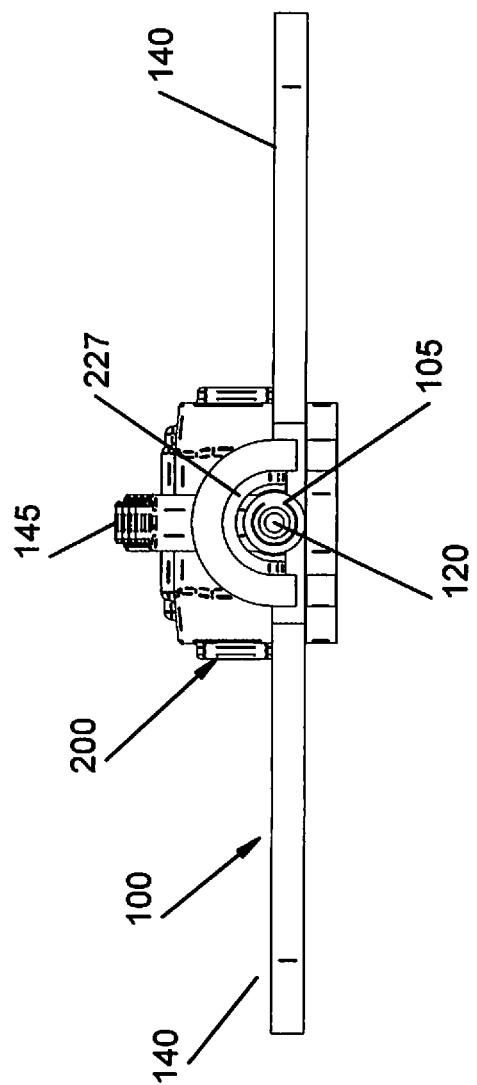
FIG. 2 is a front or needle end view of the blood collection set according to the present invention illustrating the needle in the extended position.
Figure 3:
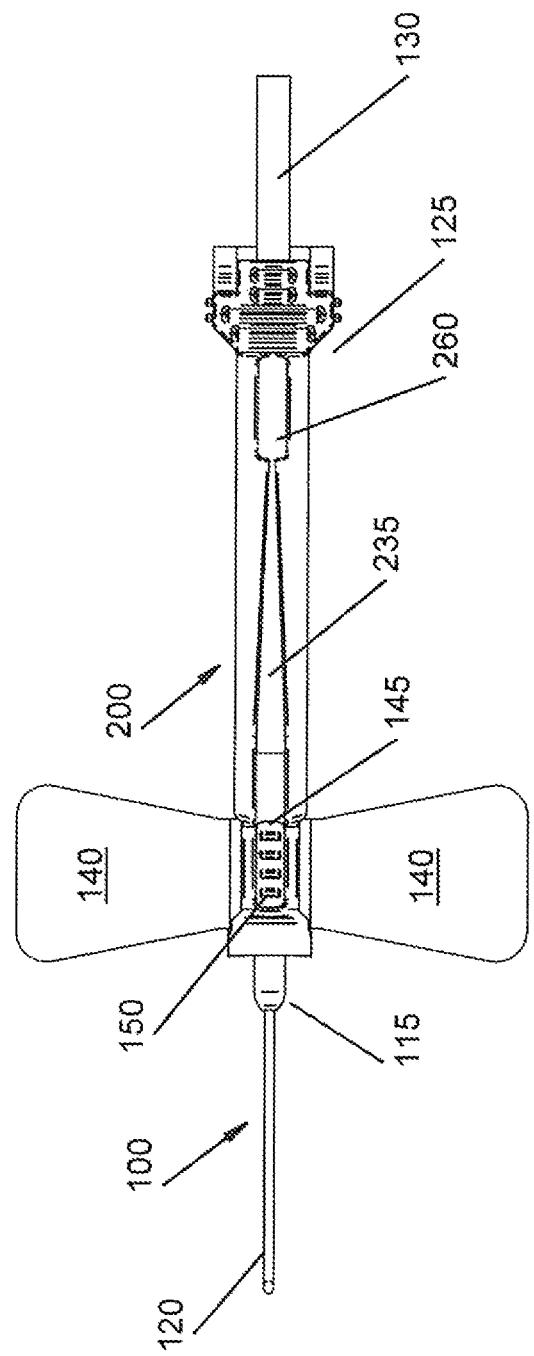
FIG. 3 is a plan view of the blood collection set according to the present invention illustrating the needle in the extended position.
Figure 4:
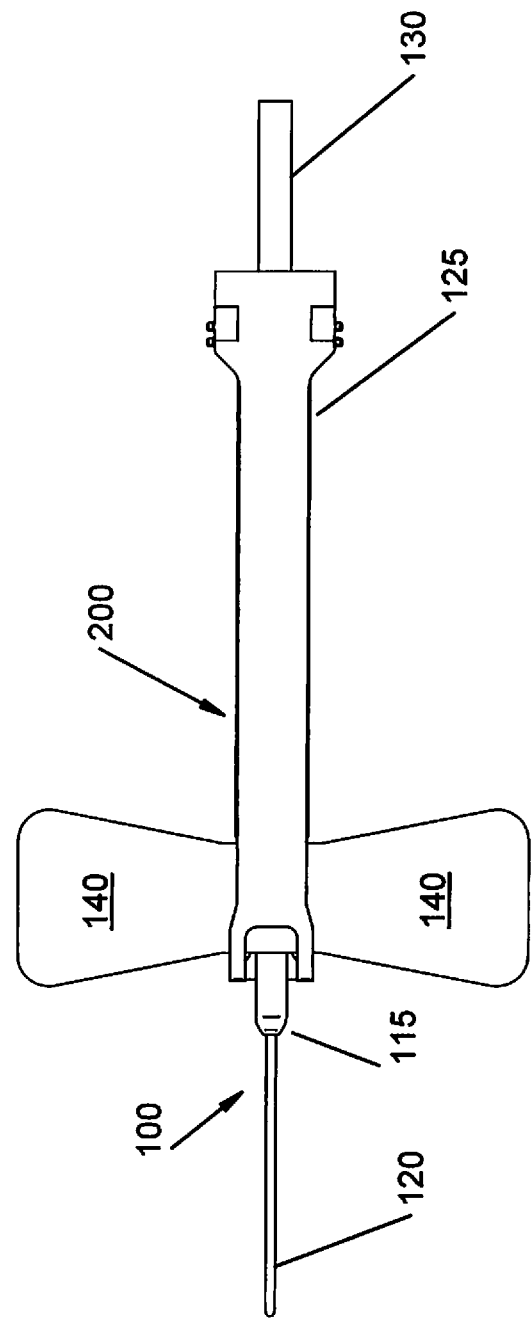
FIG. 4 is an underside view of the blood collection set according to the present invention illustrating the needle in the extended position.
Figure 5:
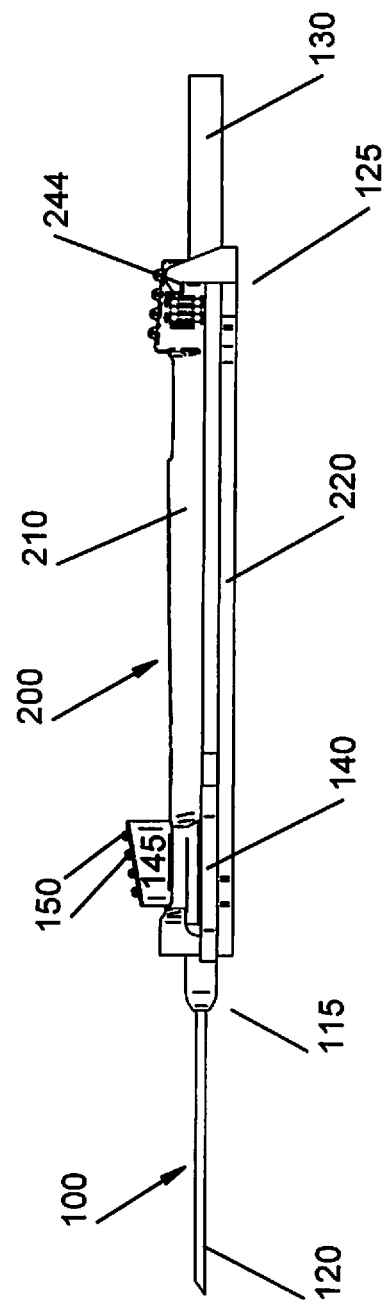
FIG. 5 is a side view of the blood collection set according to the present invention illustrating the needle in the extended position.
Figure 7:
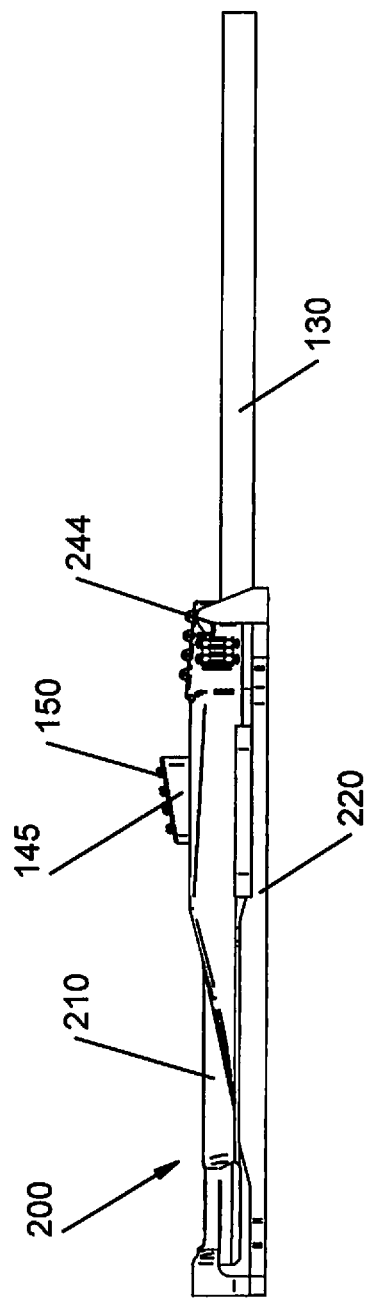
FIG. 7 is a side view of the blood collection set according to the present invention illustrating the needle in the retracted position.
Figure 8:
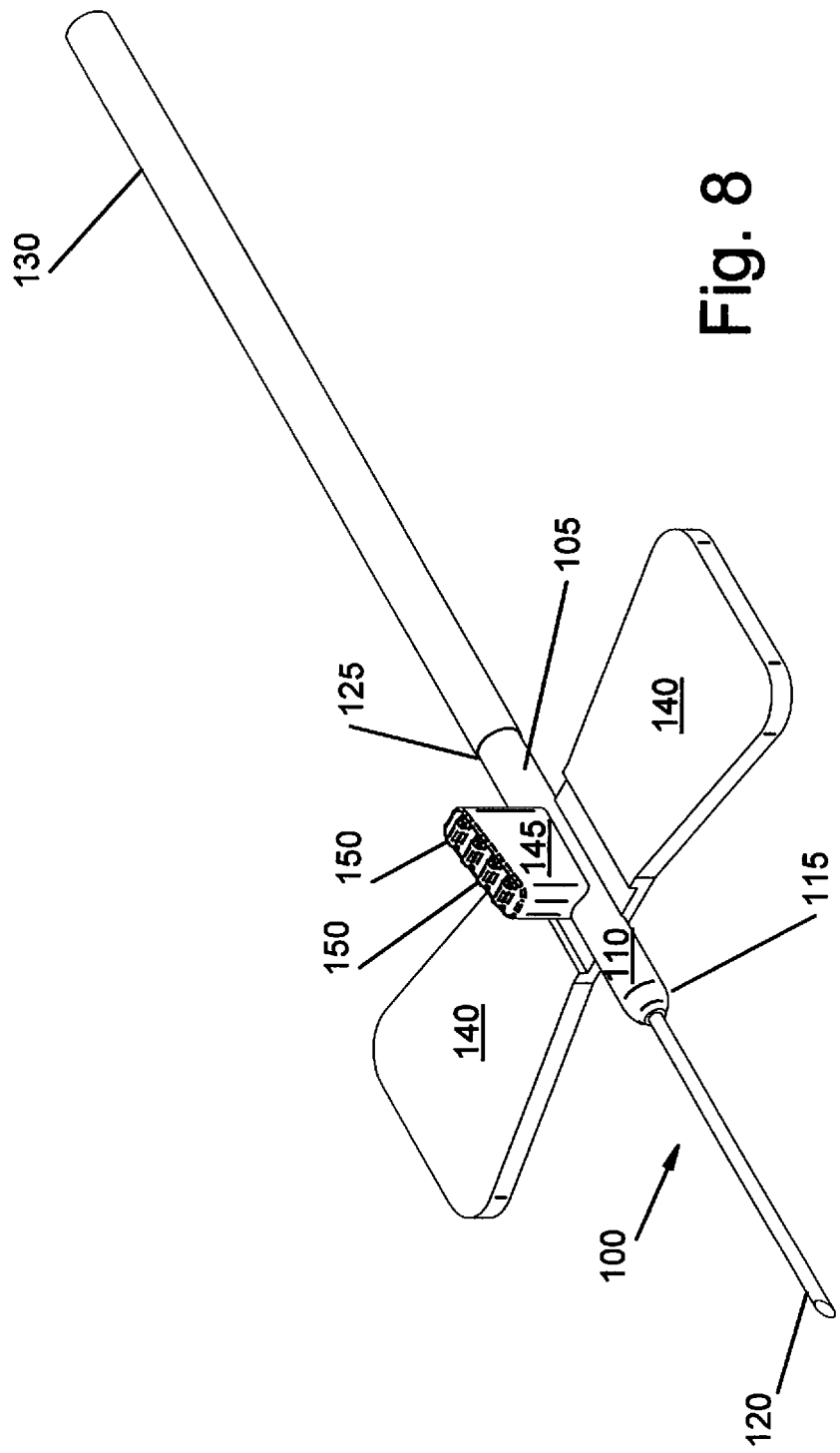
FIG. 8 is a perspective view of the wing body according to the present invention.
Figure 9:
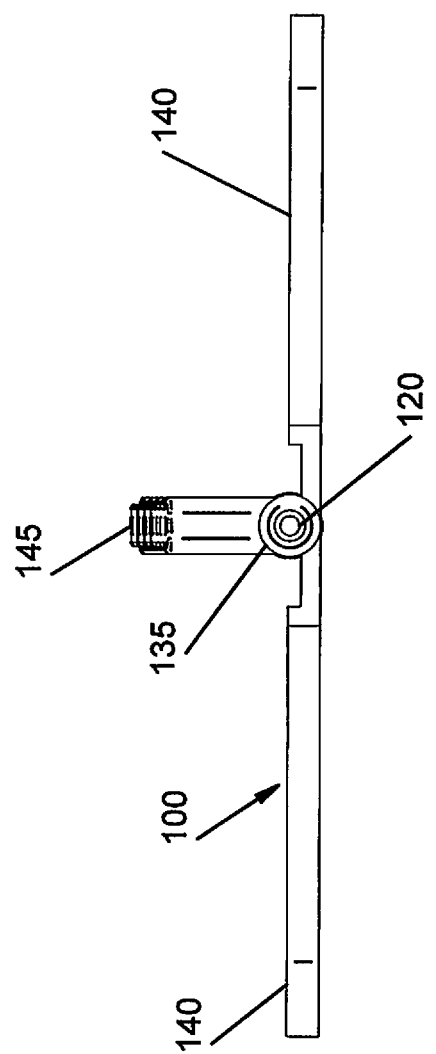
FIG. 9 is a front or needle end view of the wing body according to the present invention.
Figure 10:
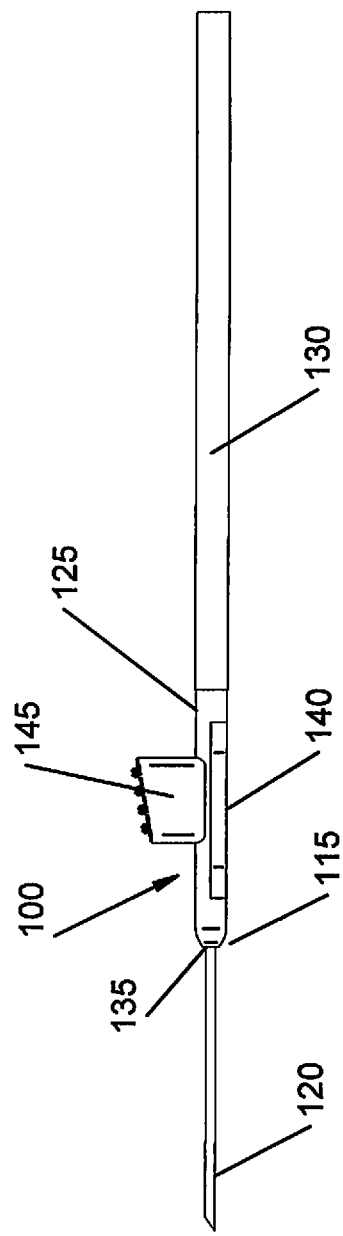
FIG. 10 is a side view of the wing body according to the present invention.
Figure 11:
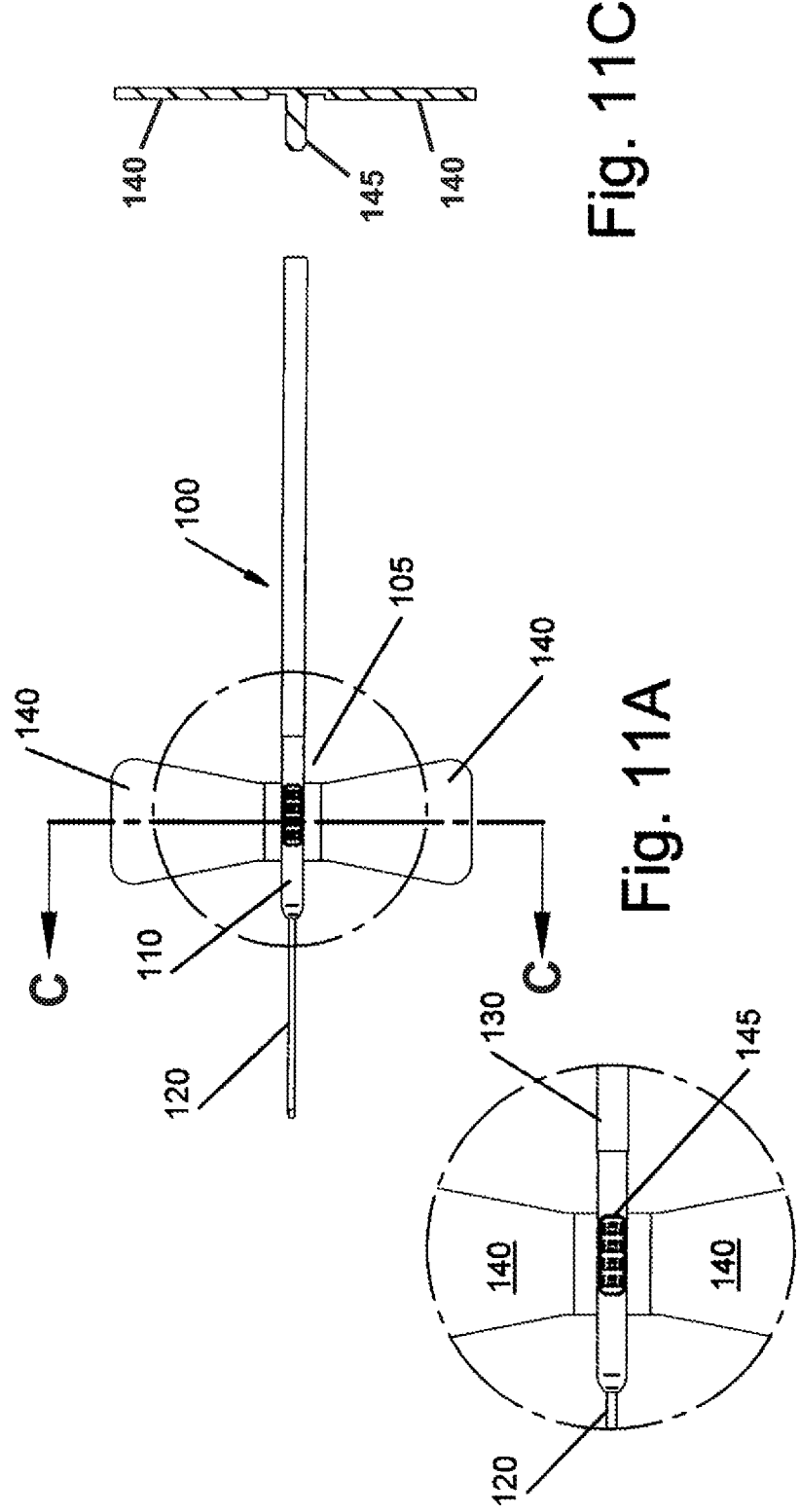
FIG. 11A is a plan view of the wing body according to the present invention.
FIG. 11B is an enlarged view of area A of FIG. 11A showing the wings and grip portions of the wing body according to the present invention.
FIG. 11C is a sectional view taken along line C-C of FIG. 11A and showing the wing body according to the present invention.
Figure 12:
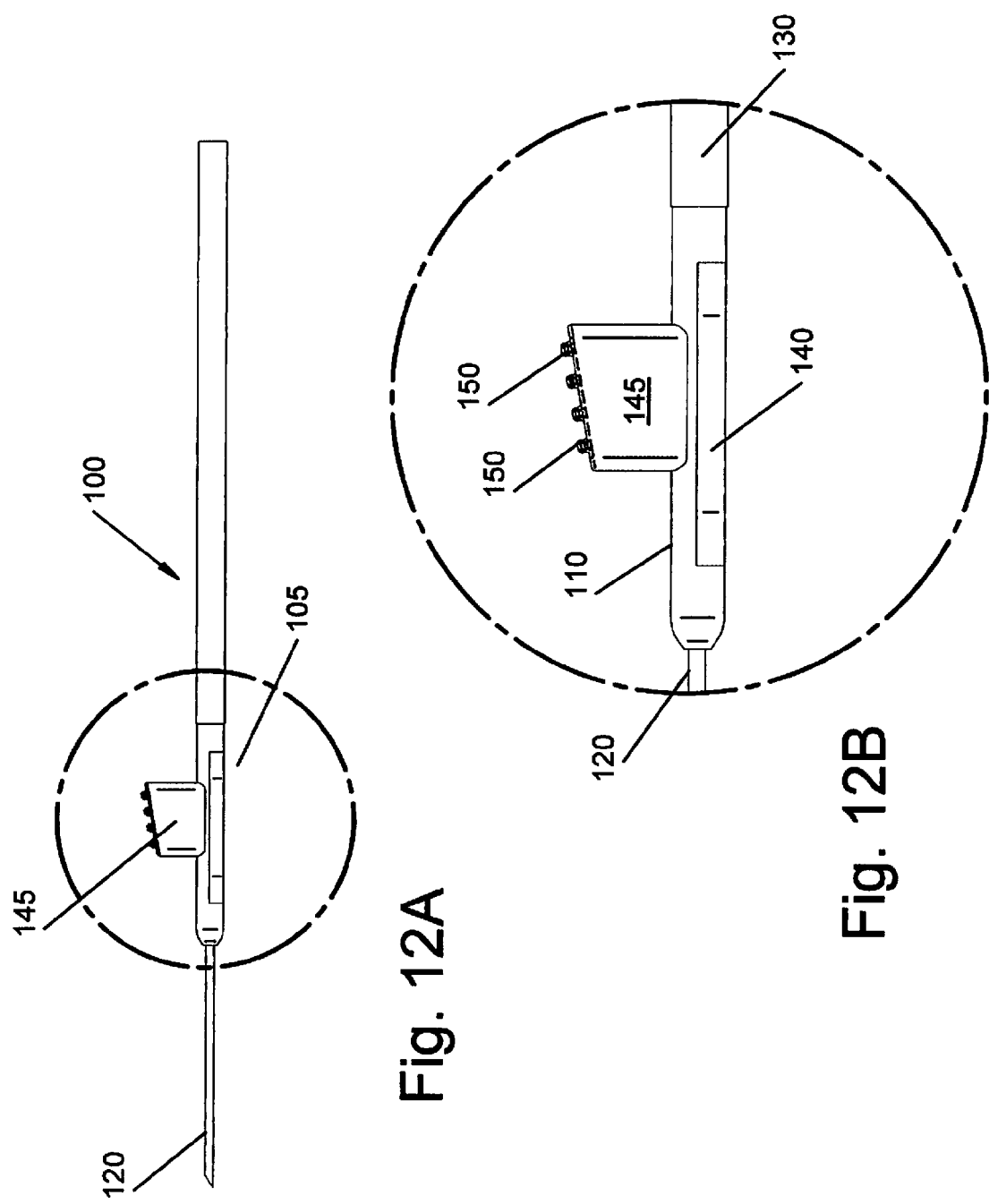
FIG. 12A is a side view of the wing body according to the present invention.
FIG. 12B is an enlarged view of area B of FIG. 12A showing the wings and grip portion of the wing body.
Figure 13:
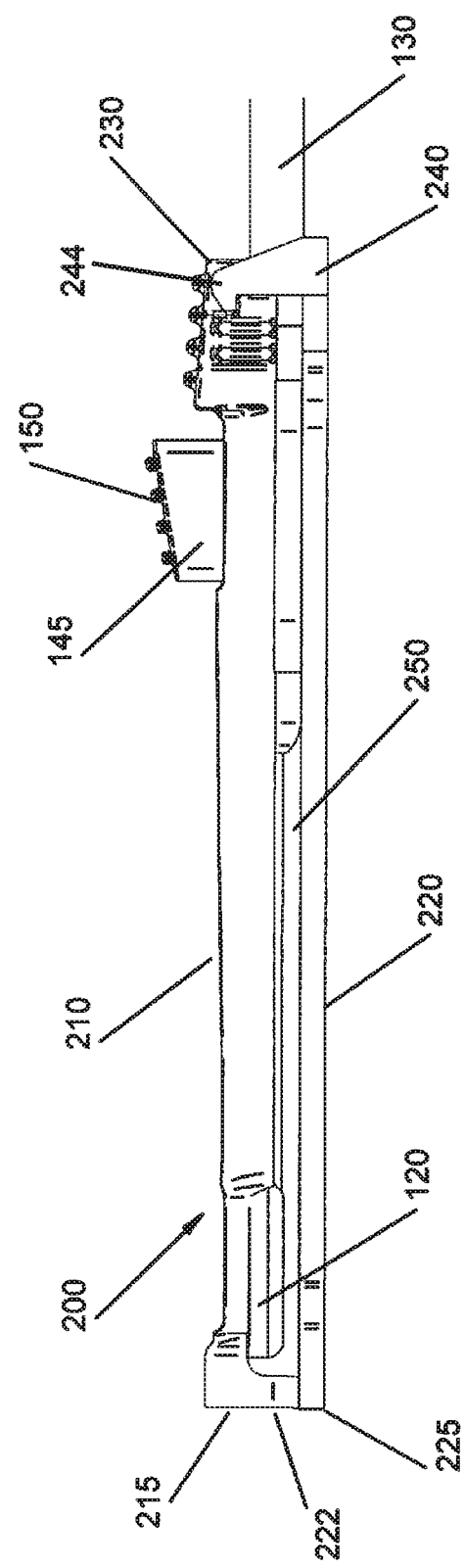
FIG. 13 is a side view of the safety shield according to the present invention in the folded and locked position.
Figure 14:
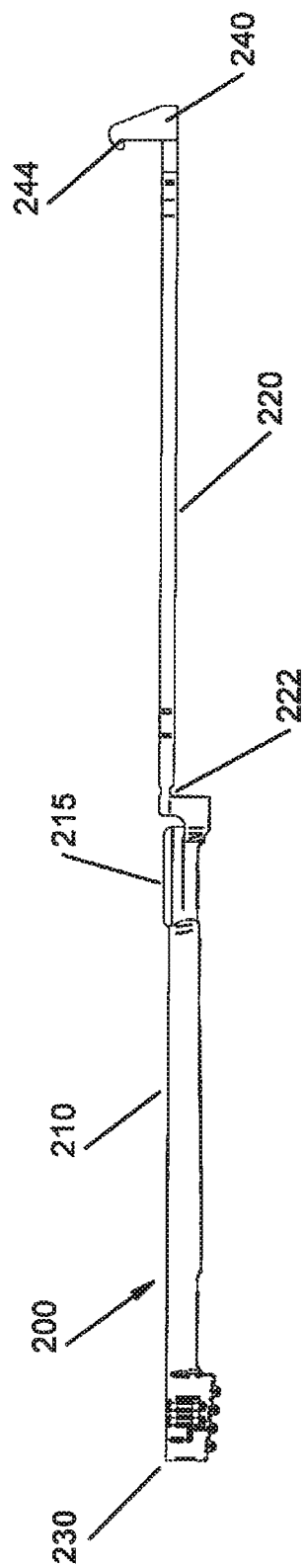
FIG. 14 is a side view of the safety shield according to the present invention in the unfolded position.
Figure 15:
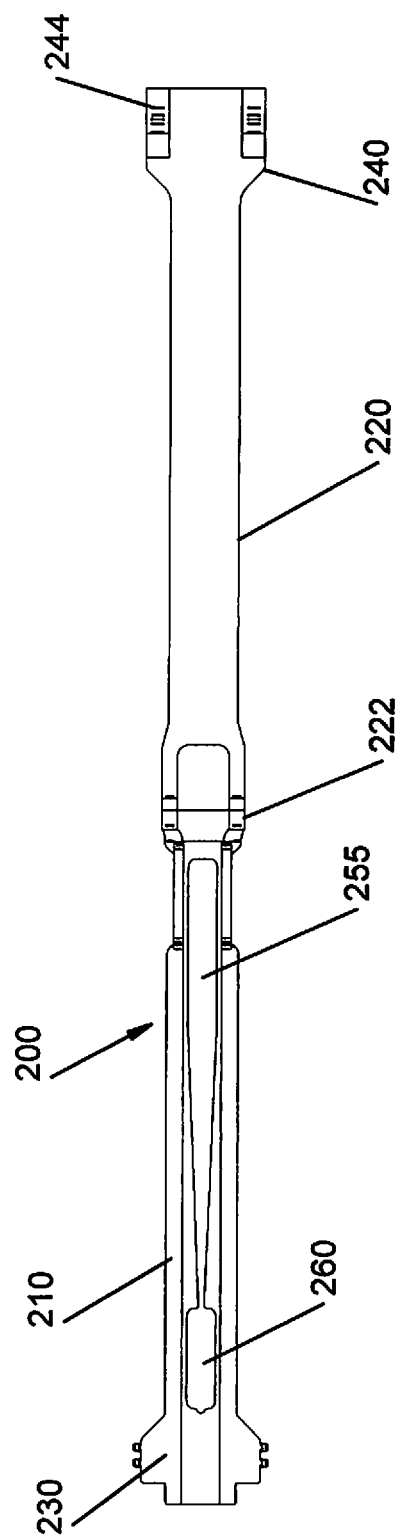
FIG. 15 is a plan view of the safety shield according to the present invention in the unfolded position.

An I.V. infusion or blood collection apparatus comprises an I.V. infusion set and a safety shield adapted to surround the I.V. infusion set or blood collection apparatus. The I.V. infusion or blood collection apparatus comprises a wing body having a central portion having a proximal end to which a needle is connected and a distal end to which tubing is connected. Also provided is a bore extending through the wing body to permit the flow of fluid between the needle and the medical tubing. The wing body includes a pair of substantially coplanar wings extending horizontally outward from the opposite sides of the central portion and a grip extending upwardly from the central portion substantially perpendicular to the wings.

The safety shield is adapted to surround the wing body and comprises a lower shield section adapted to overlie the patient's skin and an upper shield section. The respective lower shield section and the upper shield section are hingedly connected at a first end and adapted to be connected to each other at the respective opposite ends to form a chamber. The chamber is adapted to receive the infusion set therein. The safety shield includes a front end through which the needle of the IV set extends for use and a rear end through which the IV infusion set tubing extends. The side walls of said safety shield include a pair of opposing slots through which the respective wings of the IV infusion set are adapted to be slidably received.

An elongate slot is positioned in the top wall of the safety shield through which the grip extends. The elongate slot includes a locking means proximate the rear end of the safety shield for maintaining the needle in a permanently locked position upon retraction of the needle into the chamber. Thus, when the pair of opposing slots and the elongate slot are of sufficient length to enable the IV infusion set to move from an operative position wherein the needle is exposed for use to a safety position wherein the needle is fully retracted into the chamber and the grip is lockingly received in the locking means.

DETAILED DESCRIPTION OF THE PREFERRED EMBODIMENT

While the present invention will be described more fully hereinafter, it is to be understood at the outset that persons of skill in the art may modify the present invention herein described while still achieving the favorable results of the invention. Accordingly the description which follows is to be understood as a broad teaching disclosure directed to persons of skill in the appropriate arts, and not as limiting upon the present invention.

For ease of reading, in the description that follows the I.V. infusion or blood collection apparatus will at times be referred to as the "BCS", blood collection set.

As shown in the figures, the BCS 50 according to the present invention comprises an I.V. infusion set 100 and a safety shield 200.

I.V. infusion set 100 comprises a wing body 105 having a central portion 110 with a proximal end 115 to which a needle 120 is connected and a distal end 125 to which tubing 130 is connected. A longitudinal bore 135 extends through the central portion 110 of wing body 105 to permit the flow of fluid between the medical tubing 130 and needle 120. Wing body 105 further includes a pair of substantially coplanar wings 140 that extend horizontally outward from opposite sides of central portion 110. A grip 145 extends upwardly from the central portion 110 substantially perpendicular to the wings 140. According to convention in the industry, the wing body 105 and wings 140 are referred to as a "butterfly". It will be noted that generally, the wings 140, central portion 110, bore 135 and grip 145 are molded as a single unit. The area where the respective wings 140 connect to wing body 105 is thinner than the wings such that the wings 140 are bendable with respect to the wing body 105. Fabrication techniques and materials for the wing body 105 are well known to those skilled in the art. Further, the needle 120 and medical tubing 130 are connected to wing body 105 by suitable means, again well known to those skilled in the art, such as glue, cyanoacrylate, heat bond or other type of bonding.

As briefly mentioned herein above, grip 145 is integrally molded with wing body 105 and extends upwardly there from between approximately 80% the width and 33% the length thereof. The top of grip 145 is angled upward from the proximal 115 end to the distal end 120 and includes a series of axially extending ridges 150 which aid in handling the BCS as will be explained in further detail herein below.

Figure 16:
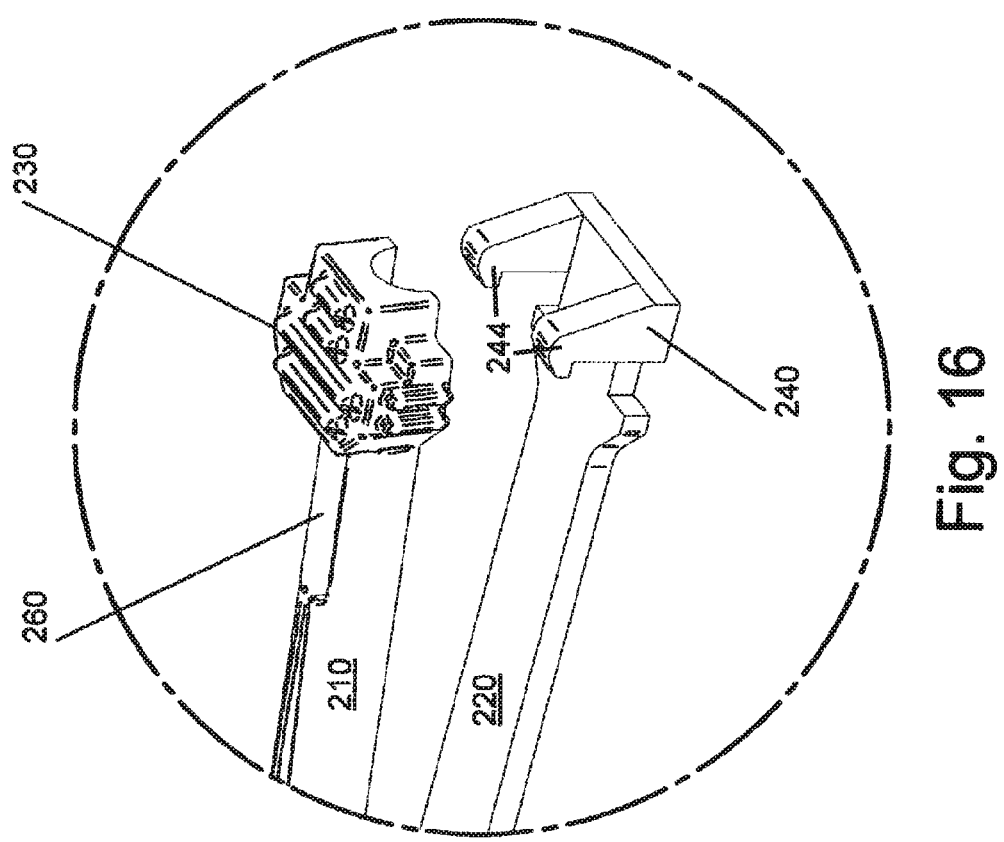
FIG. 16 is an enlarged view of the locking mechanism portion of the safety shield according to the present invention.
Figure 17:
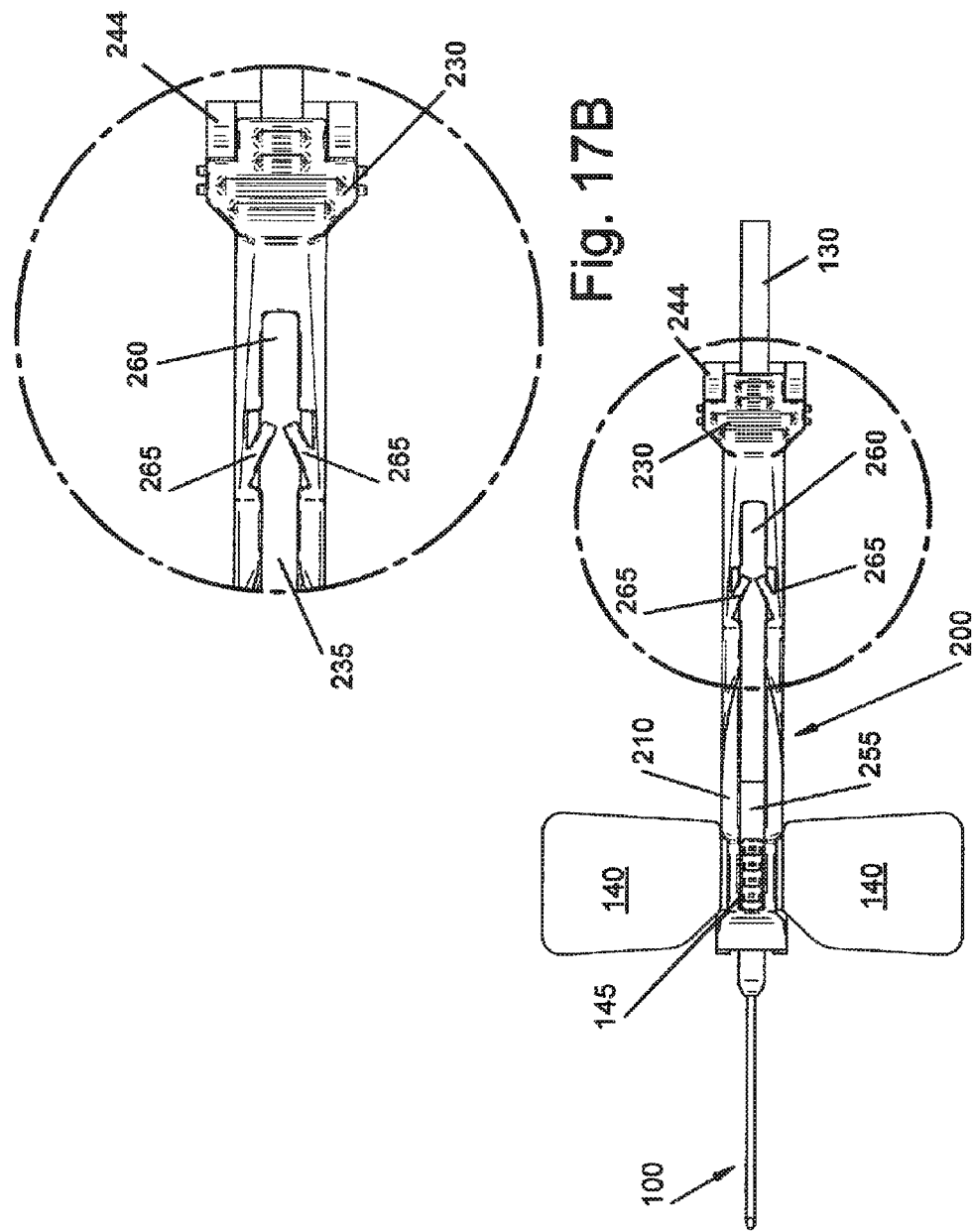
FIG. 17A is a plan view of a second embodiment of the present invention and illustrating an alternate embodiment of the locking mechanism with the needle in the extended position.
FIG. 17B is an enlarged view of the locking mechanism of FIG. 17A according to the present invention.
Figure 18:
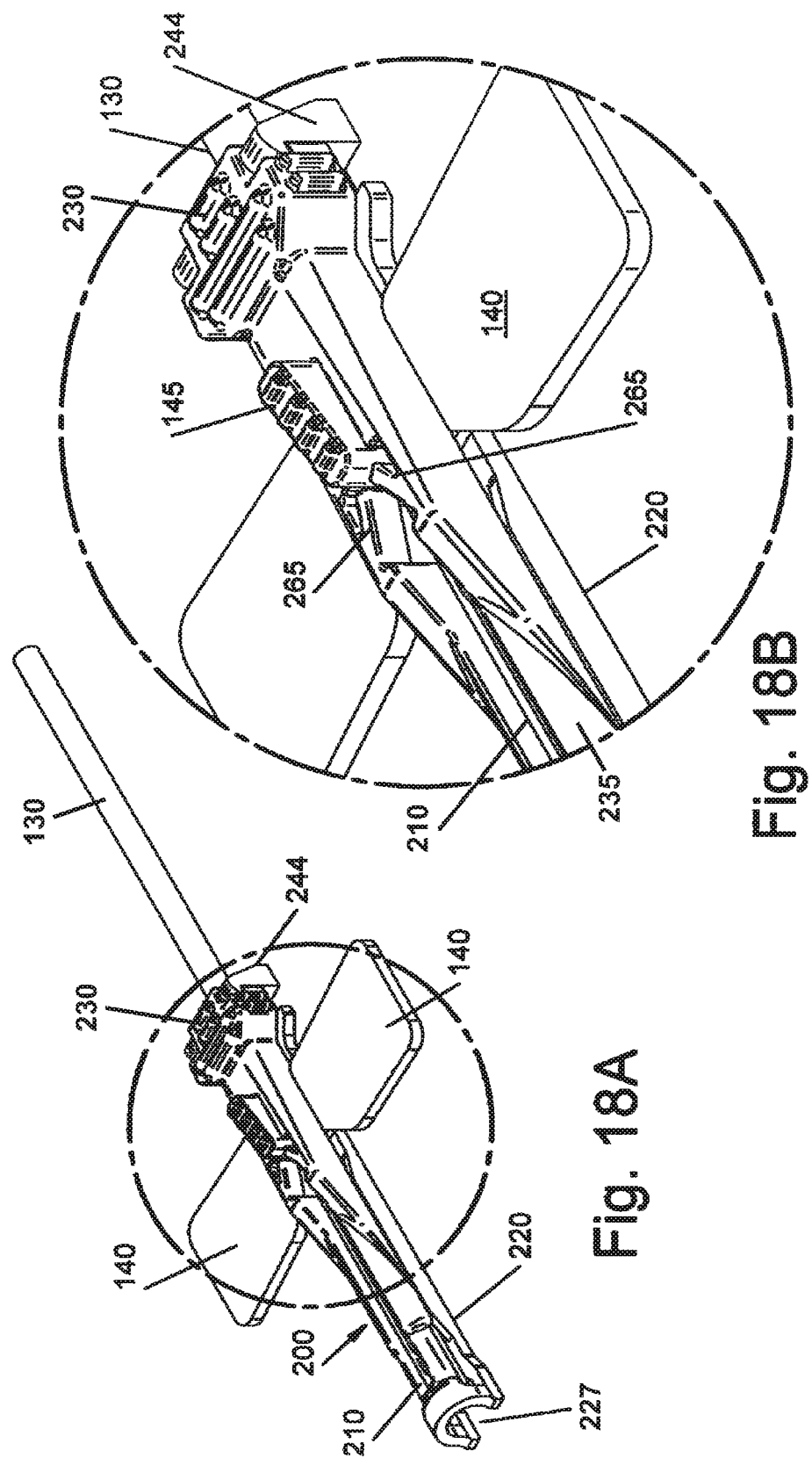
FIG. 18A is a perspective view of the second embodiment of the present invention and showing the needle in the retracted safety position with the grip in locked position.
FIG. 18B is an enlarged view of the locking mechanism with the needle retracted in the safety position with the grip in the locked position.
Figure 19:
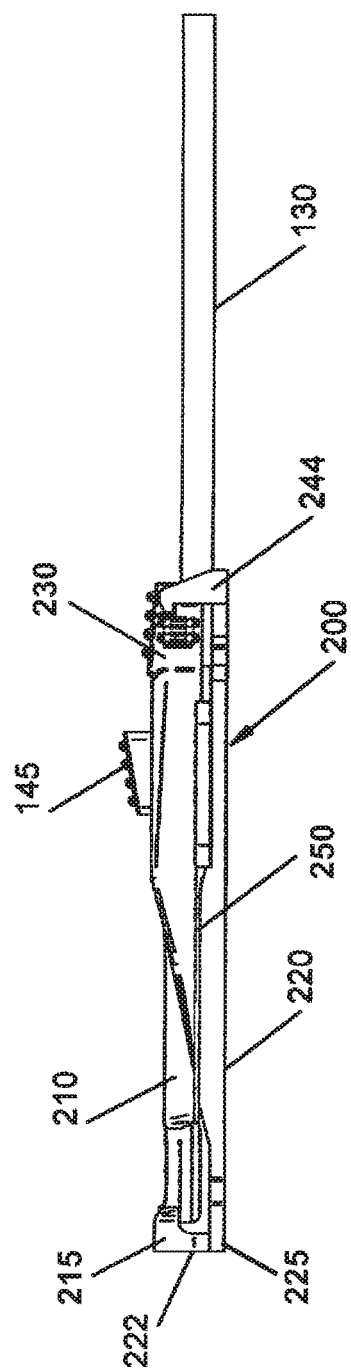
FIG. 19 is a side view of the second embodiment of the present invention and showing the needle in the retracted position with the grip locked.
Figure 20:
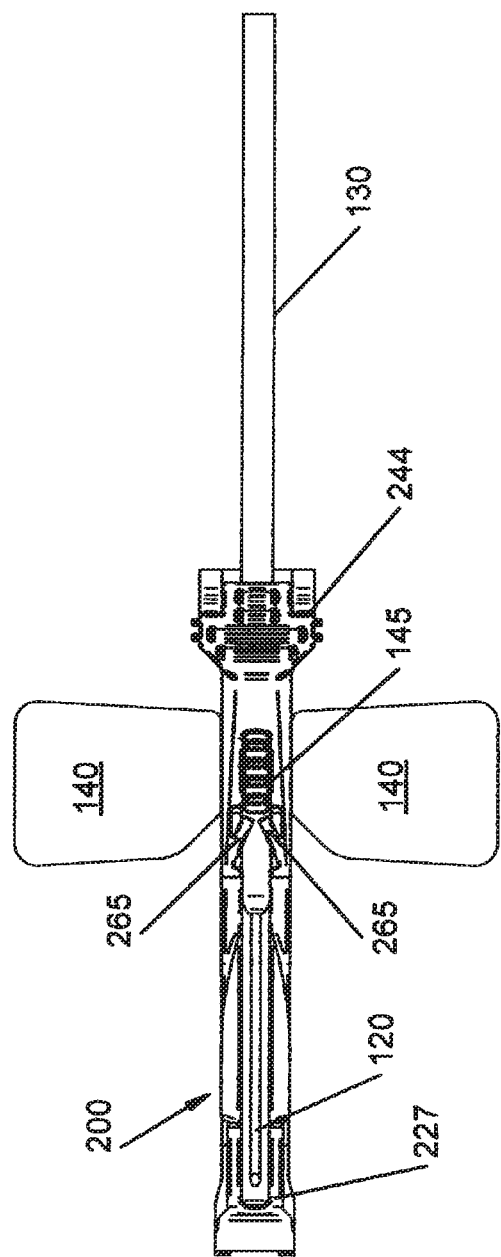
FIG. 20 is a plan view of the second embodiment of the present invention showing the needle in the retracted position with the grip locked.
Figure 21:
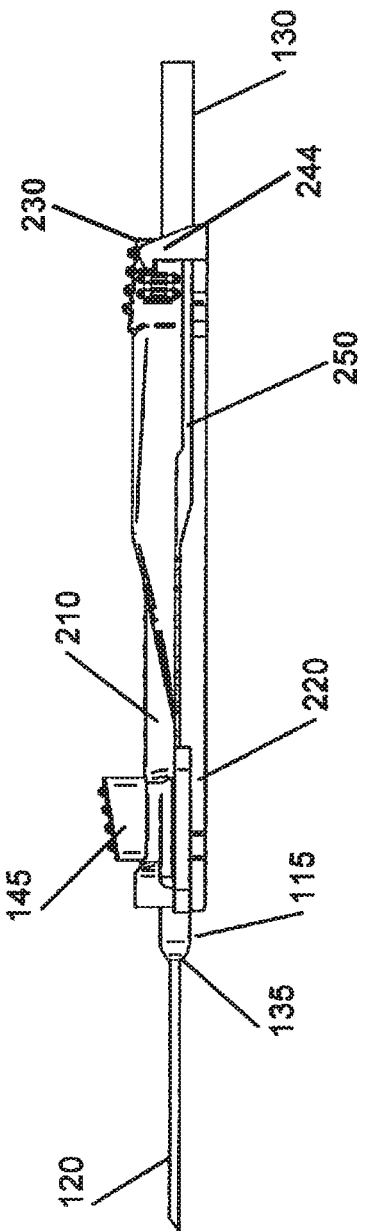
FIG. 21 is a side view of the second embodiment of the present invention showing the needle in the extended position.

Safety shield generally indicated at 200 is adapted to overlie the patient's skin and comprises an upper shield section 210 having a first hinge end 215 and a lower shield section 220 having a second hinge end 225 that are adapted to be connected together to form a chamber 227. In the illustrated embodiment, the respective first and second ends 215, 225 terminate in living hinge 222 and the respective opposite upper shield end 230 and lower shield opposite end 240 are adapted to be snapped together as best shown in FIG. 16. The snap closure 244 is a standard cantilever beam type of snap fit connection. Those skilled in the art will note that other types of closure mechanisms may be employed such as a post and hold, glue together method or other types of closures, well known to those skilled in the art.

The sides of the safety shield are contoured to form elongate slots or grooves 250 in opposite sides thereof when the respective shield sections 210, 220 are connected to form chamber 227. Additionally, an elongate longitudinal slot 255 is located in upper shield section 210 and terminates in a widened zone 260 which acts to lock the I.V. infusion set in the locked position after use. In another embodiment of the invention, the terminating end of slot 255 additionally includes a pair of flexible "fingers" 265, which extend from the opposite sides of slot 235 and point towards the medical tubing end of the safety shield 200 and collectively form a locking means for maintaining the I.V. infusion set in a locked position after use. It will be noted that the rear end of the safety shield 200 should be of sufficient length to enable single handed retraction of the needle 120 into the "safety" or locked position. More specifically, the distance from the tubing end of the safety shield 200 to the terminating end of the locking means should be long enough to permit the safety shield to be gripped with the thumb and middle finger of the user while the pointer finger engages the needle end of the grip 145 and slides the needle 120 into the safety shield 200 until the locking means fully engages the grip whereupon the needle 120 will be fully retracted and permanently locked within the safety shield 200 for safe disposal.

Elongate slots 250 and 255 are constructed and arranged to enable the wings 140 of the I.V. infusion set 100 to move from an operative position wherein the needle 120 is exposed for use to a safety position wherein the needle 120 is fully retracted into the chamber 227. Upon full retraction, the wings 140 are positioned proximate the tubing end of the safety shield 200 and the grip 145 is lockingly received in the locking means portion of the elongate slot 255 in the top wall 210 of the safety shield 200.

While certain illustrative embodiments have been described, it is evident that many alternatives, modifications, permutations and variations will become apparent to those skilled in the art in light of the foregoing description.

That which is claimed is:

1. An I.V. infusion or blood collection apparatus, comprising:
    an I.V. infusion set, comprising:
        a wing body having a central portion having a proximal end to which a needle is connected, a distal end to which tubing is connected, and further including a bore therethrough to permit a flow of fluid between said needle and said tubing, and wherein the wing body includes a pair of flexible opposing wings extending outward from said central portion in at least one first direction, wherein said central portion includes a grip extending outward from said central portion in a second direction; and
    a safety shield constructed and arranged to surround said wing body and comprising;
        a lower shield section adapted to overlie a patient's skin;
        an upper shield section, said lower shield section and said upper shield section adapted to be connected at a first end and adapted to be connected to each other at respective opposite ends to form a chamber, said chamber having a top, a bottom, and opposing side walls, said safety shield being adapted to receive within said chamber said central portion of the wing body, said safety shield including a front end through which the needle of the I.V. infusion set is extendable for use, and said safety shield including a rear end through which the I.V. infusion set tubing extends; and
        a pair of opposing slots in the respective opposing side walls of said safety shield through which respective wings of the pair of flexible opposing wings of said I.V. infusion set are adapted to be positioned for slidable movement; and
        an elongate slot in the top wall of the chamber of said safety shield through which said grip is adapted to be positioned for slidable movement of said central portion;
        wherein said pair of opposing slots and said elongate slot are constructed and arranged to enable said I.V. infusion set to move from an operative position in which said needle is exposed for use to a safety position in which said needle is fully retracted into said chamber; and
        wherein said grip is configured for unimpeded slidable movement within the elongate slot from the operative position towards the safety position.

2. The I.V. infusion or blood collection apparatus according to claim 1, further comprising:
    a lock member configured to lock said I.V. infusion set in the safety position, wherein the lock member is operatively associated with said elongate slot in the top wall and is positioned proximate a rear end of the elongate slot,
    whereby upon movement of said I.V. infusion set to the safety position, the grip is configured to be engaged by the lock member, and the needle is configured to permanently lock within said chamber.

3. The I.V. infusion or blood collection apparatus according to claim 2, wherein said lock member comprises a pair of flexible fingers extending from opposite sides of said slot, and wherein said pair of flexible fingers point towards the rear end of the safety shield.

4. The I.V. infusion or blood collection apparatus according to claim 1, wherein said grip is substantially perpendicular to said pair of flexible opposing wings.

5. The I.V. infusion or blood collection apparatus according to claim 1, wherein said lower shield section and said upper shield section are connected at one end with a living hinge.

6. The I.V. infusion or blood collection apparatus according to claim 1, wherein said elongate slot is tapered, including a wide end proximate the front end of said safety shield and including a narrow end proximate the rear end of the safety shield.

7. The I.V. infusion or blood collection apparatus according to claim 6, wherein the narrow end of said elongate slot terminates at a locking member adapted to lock said I.V. infusion set in the safety position, and
    wherein upon movement of said I.V. infusion set to the safety position, the grip is engaged by the locking member and the needle is permanently locked within said chamber.

8. The I.V. infusion or blood collection apparatus according to claim 1, wherein the pair of flexible opposing wings extends horizontally outward from said central portion.

9. The I.V. infusion or blood collection apparatus according to claim 8, wherein said elongate slot comprises a locking member positioned at one end of said elongate slot and adapted to lockingly receive said grip.

10. The I.V. infusion or blood collection apparatus according to claim 9, wherein said locking member further includes a pair of flexible fingers extending from opposite sides of said elongate slot, and wherein said pair of flexible fingers point towards the rear end of the safety shield.

11. The I.V. infusion or blood collection apparatus according to claim 1, further comprising a locking member adapted to lock said needle in the safety position, wherein said locking member is operatively associated with said elongate slot.

12. The I.V. infusion or blood collection apparatus according to claim 1, wherein the I.V. infusion set is unlocked when the I.V. infusion set is positioned in the operative position and the needle is exposed for use.

13. A method of using an I.V. infusion or blood collection apparatus according to claim 1 for transferring fluid to or from a patient's arm or vein, the method comprising:
   moving the grip of the I.V. infusion set within the elongate slot of the safety shield forward toward the front end of the safety shield;
   gripping the pair of flexible opposing wings with one hand; and
   guiding the needle into a patient's arm or vein while the pair of flexible opposing wings is gripped with the one hand.

14. The method according to claim 13, further comprising:
   gripping the safety shield with the one hand;
   moving the grip of the I.V. infusion set within the elongate slot of the safety shield backward toward the rear end of the safety shield with a finger of the one hand to remove the needle from the patient's arm or vein.

15. The method according to claim 13, further comprising locking said I.V. infusion set in the safety position utilizing a locking member operatively associated with said elongate slot and being positioned proximate the rear end thereof, whereby upon movement of said I.V. infusion set to the safety position, the grip is engaged by the locking member and the needle is permanently locked within said chamber.

16. The method according to claim 15, wherein said locking member comprises a pair of flexible fingers extending from opposite sides of said elongate slot, and wherein said pair of flexible fingers point towards the rear end of the safety shield.

17. The method according to claim 13, wherein said grip is substantially perpendicular to said pair of flexible opposing wings.

18. The method according to claim 13, wherein said lower shield section and said upper shield section are connected at one end with a living hinge.

19. The method according to claim 13, wherein said elongate slot is tapered, including a wide end proximate the front end of said safety shield and including a narrow end proximate the rear end of the safety shield.

20. The method according to claim 19, wherein the narrow end of said elongate slot terminates at a locking member adapted to lock said I.V. infusion set in the safety position, and wherein upon movement of said I.V. infusion set to the safety position, the grip is engaged by the locking member and the needle is permanently locked within said chamber.

21. The method according to claim 13, wherein the I.V. infusion set is unlocked when the I.V. infusion set is positioned in the operative position and the needle is exposed for use.

* * * * *